(12) United States Patent
Thibodo, Jr.

(10) Patent No.: US 6,503,216 B1
(45) Date of Patent: Jan. 7, 2003

(54) PALM SPLINT SYSTEM

(76) Inventor: Calvin Thibodo, Jr., 1061 Grandview Blvd., Kansas City, KS (US) 66102

( * ) Notice: Subject to any disclaimer, the term of this patent is extended or adjusted under 35 U.S.C. 154(b) by 0 days.

(21) Appl. No.: 09/655,689

(22) Filed: Sep. 6, 2000

(51) Int. Cl.[7] ............................. A61F 5/00; A61F 9/00
(52) U.S. Cl. ................................................ 602/21; 2/16
(58) Field of Search ...................... 602/20–21, 60–62, 602/64, 13, 5, 14; 128/878, 879; 2/16, 161.2, 161.1; D29/113, 115, 116.1–116.2, 120.1; 473/59, 62, 212, FOR 106

(56) References Cited

U.S. PATENT DOCUMENTS

| | | | | |
|---|---|---|---|---|
| 2,952,021 A | * | 9/1960 | Finn | 2/16 |
| 3,496,573 A | * | 2/1970 | Kuchar et al. | 2/161 |
| 3,606,614 A | * | 9/1971 | Dimitroff | 2/159 |
| 3,703,728 A | * | 11/1972 | Saunders et al. | 2/16 |
| 3,818,905 A | * | 6/1974 | Lebold | 128/77 |
| 4,103,682 A | | 8/1978 | Franzl | |
| 4,270,228 A | * | 6/1981 | Gaiser | 2/158 |
| 4,496,151 A | * | 1/1985 | Tureaud | 273/54 B |
| 4,765,320 A | | 8/1988 | Lindemann et al. | |
| 4,781,178 A | | 11/1988 | Gordon | |
| 4,862,877 A | | 9/1989 | Barber | |
| 5,027,802 A | | 7/1991 | Donohue | |
| 5,081,715 A | * | 1/1992 | Mascia | 2/20 |
| 5,267,945 A | | 12/1993 | Doctor et al. | |
| 5,333,605 A | | 8/1994 | Matsumura et al. | |
| D363,146 S | * | 10/1995 | Pando | D29/113 |
| 5,725,490 A | | 3/1998 | Conran | |
| D404,175 S | * | 1/1999 | Griffin, Sr. | D29/113 |
| 5,947,915 A | | 9/1999 | Thibodo, Jr. | |
| 6,200,284 B1 | * | 3/2002 | Flick | 602/13 |

* cited by examiner

Primary Examiner—Denise M. Pothier
(74) Attorney, Agent, or Firm—Kenneth W. Iles

(57) ABSTRACT

A splint system for the palm of the hand includes a splint body includes a splint body in the form of a block having an outwardly curving rear surface that is pressed against the palm of a patient's palm and fastened thereto by a strap secured to itself by hook and loop fasteners.

3 Claims, 2 Drawing Sheets

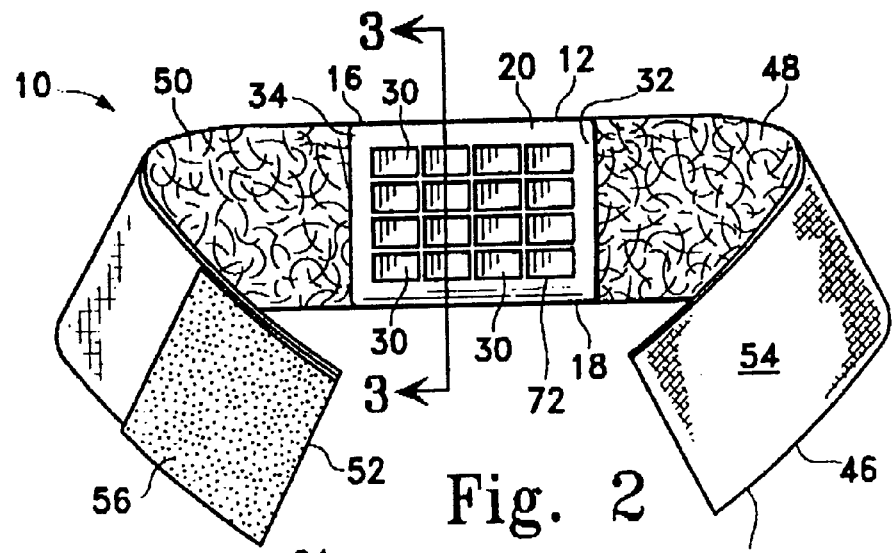
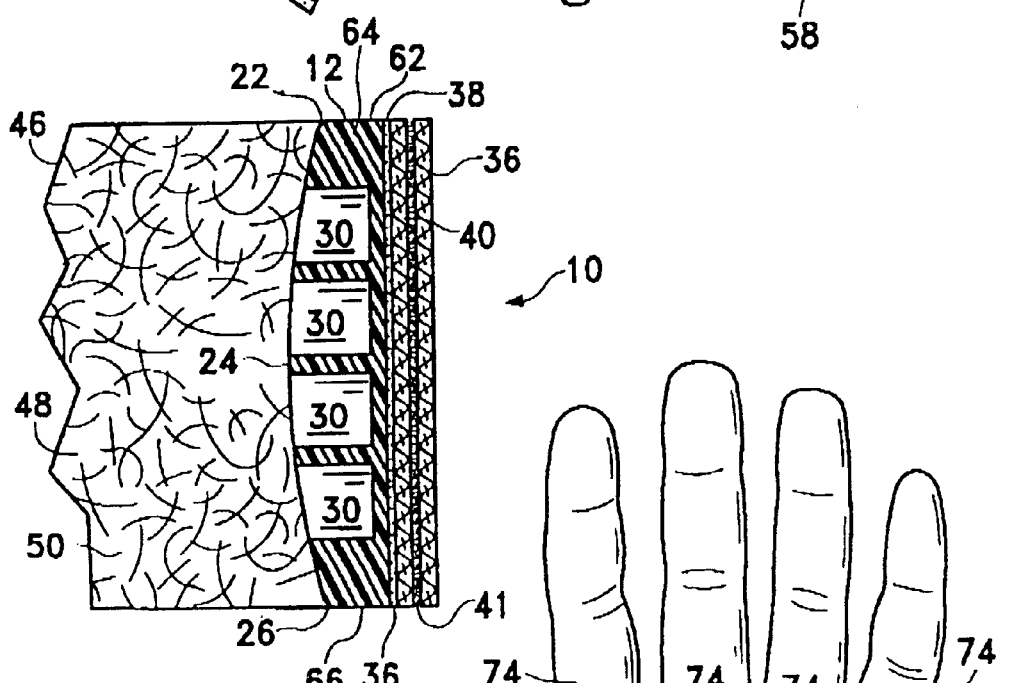
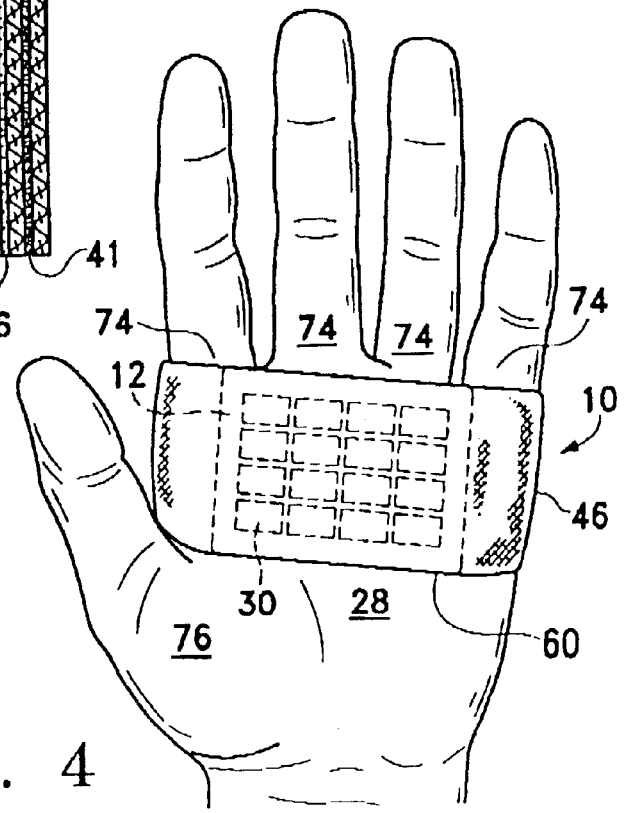
Fig. 2
Fig. 3
Fig. 4

PALM SPLINT SYSTEM

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention is related to an apparatus for splinting the palm of the hand. More particularly, the present invention is directed to a splinting system that includes a firm body pressed against the palm.

2. Description of Related Art Including Information Disclosed Under 37 C.F.R. Sections 1.97–1.99.

Injuries to fingers and hands are common and typical causes include trauma causing broken bones, strained ligaments and tendons and the like, carpal tunnel syndrome, repetitive motion injury, and the like. Frequently treatment requires that the affected finger or fingers be immobilized with a splint. Treatment can also include splinting the palm to provide a means for relaxing the ligaments and tendons in the palm, which are connected at one end to various points on the fingers and at their other ends to muscles or bones in the forearm. It has been found that providing moderate pressure against the palm provides relief from pain and allows activities that would have been uncomfortable or dangerous without a palm splint, such as typing when suffering the symptoms of carpal tunnel syndrome caused by too much typing or improper typing techniques. The early stages of carpal tunnel syndrome, sometimes called repetitive motion injury, caused by other types of work, for example, certain work in meat packing, assembly line work and the like, can also be treated and the pain alleviated by a palm splint.

In other situations, a palm splint is used to restrain the fingers from curling excessively into the palm, which, particularly in older patients, can exacerbate a tendency for the tendons to shorten and which results in permanent cramping of the fingers.

Prior art splints are typically either very simple or very complex and mostly provide splinting for the fingers. Simple finger splints include, for example, straight flat wooden or metal sticks that are bound to the affected fingers.

Other simple splints are formed from bent metal, such as aluminum, and may include an elongated trough shape designed to fit more closely to the finger and may include a curved upper end designed to protect a finger tip. Foam padding may be attached to the inner surface of such a splint. This type of splint, however, is also devoted to splinting a finger without providing any support for the portions of the palm that include ligaments that run to the affected finger or fingers.

More complex splints are very complicated and have many parts, such as Lindemann et al. U.S. Pat. No. 4,756, 230, Gordon U.S. Pat. No. 4,781,178 and Donohue U.S. Pat. No. 5,027,802. Lindemann '320, for example, includes a collar applied over each finger and are connected to a forearm band by an elastic band, but there is little if any splinting effect in the palm. Gordon '178 discloses an orthopedic glove with one or more splints affixed at selective locations to immobilize and join and/or the wrist of the hand and is designed to immobilize particular joints having arthritis, but again, there is little or no splinting in the palm area. Donohue '802 discloses a traction system for fingers that includes a traction element under the fingers or hand. All of these devices are complex, expensive and adapted to highly specific and relatively unusual finger problems. They are not suitable for more typical strains and do nothing to support or relax the palm.

Conran, U.S. Pat. No. 5,725,490, discloses a wrist brace consisting of a fitted sleeve that fits over the patient's wrist and the lower portion of the palm and that is fastened by closing a zipper that passes lengthwise along the device down the center on the inside of the hand. The device is made of an elastic material and stiffens the wrist. It is not designed for splinting the palm.

Barber, U.S. Pat. No. 4,862,877, discloses a hand splint for supporting the wrist and includes a round cross section strap that passes between the thumb and first finger and crosses the palm. This device stiffens the wrist but provides no support to the palm.

The splints discussed above do not provide any splinting of the palm.

Therefore, there is a need for a palm splint system that easily provides relaxing support for the palm; that allows the force of the splint against the palm to be readily and easily adjusted; and that allows the patient full movement of the fingers.

BRIEF SUMMARY OF THE INVENTION

Accordingly, it is a primary object of the present invention to provide a palm splint system that easily provides relaxing support for the palm.

It is another object of the present invention to provide a palm splint system that allows the force of the splint against the palm to be readily and easily adjusted.

It is another object of the present invention to provide a palm splint system that allows the patient full range of movement of the fingers.

These and other objects of the invention are achieved by providing a solid rounded block or splint body fitted into the palm with a pad on the front and back of the splint body to provide a more comfortable feel and to absorb perspiration. The splint is fastened to the palm by a strap having hook and loop fasteners on it to permit easy adjustment of the force with which the splint is pressed against the palm. The body includes a plurality of cells that are voids. These voids reduce the mass of the splint and allow for cooling of an injection molded splint without warping.

Other objects and advantages of the present invention will become apparent from the following description taken in connection with the accompanying drawings, wherein is set forth by way of illustration and example, the preferred embodiment of the present invention and the best mode currently known to the inventor for carrying out his invention.

BRIEF DESCRIPTION OF THE SEVERAL VIEWS OF THE DRAWING

FIG. 2 is a front elevation of the palm splint of FIG. 1.

FIG. 3 is a side elevation, partially in section, of the palm splint of FIG. 1.

FIG. 4 is a front elevation of the palm splint of FIG. 1 shown in use on a patent's hand.

DETAILED DESCRIPTION OF THE INVENTION

Figure 1:
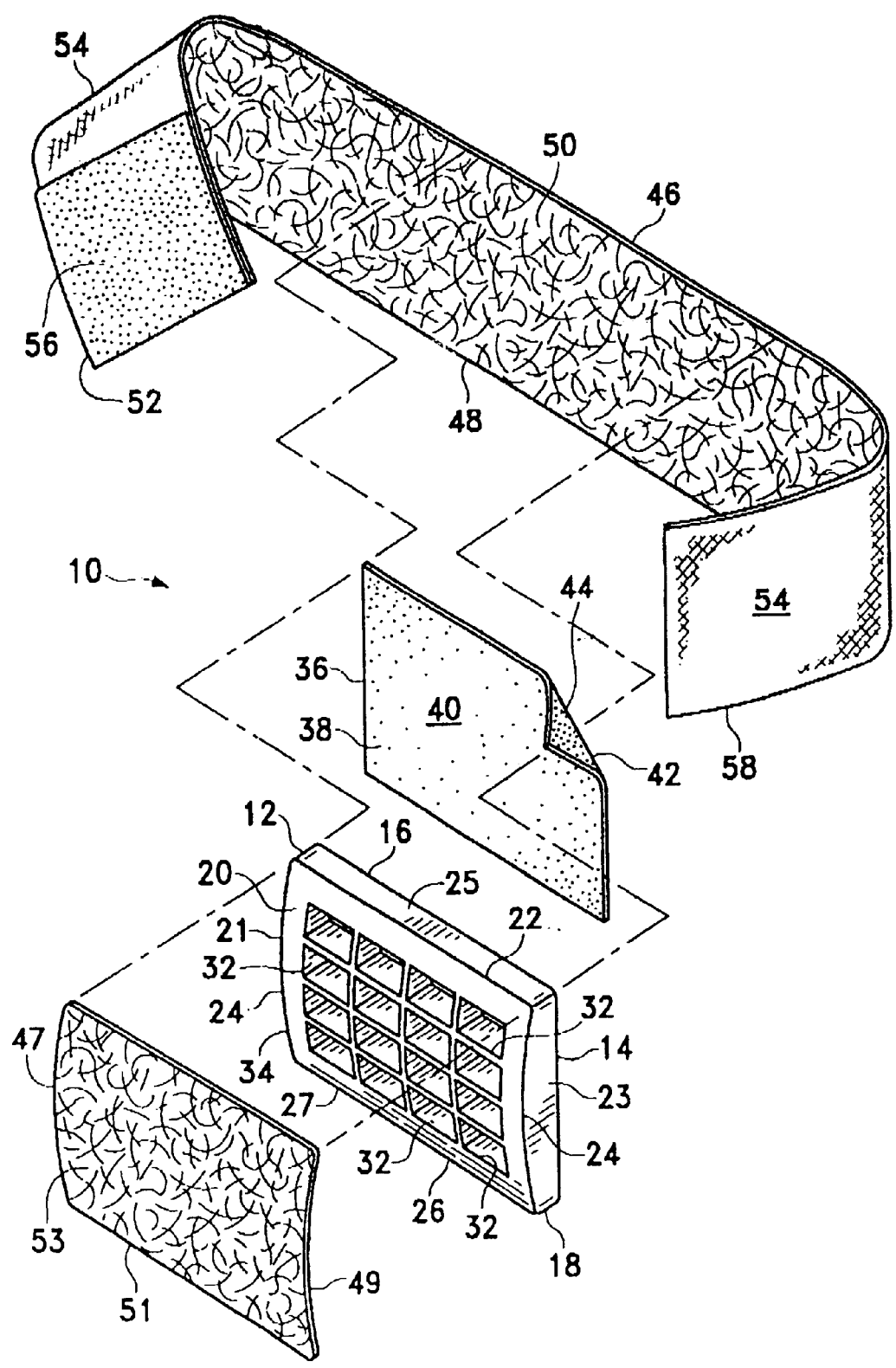
FIG. 1 is a right-hand exploded perspective view of a palm splint according to the present invention.

As required by the Patent Statutes and the case law, the preferred embodiment of the present invention and the best mode currently known to the inventor for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus disclosed herein as embodied in any appropriately specific and detailed structure.

Referring now to FIG. 1, there is shown a right-hand perspective exploded view of a palm splint 10 according to the present invention, including a splint body 12 having a flat planar front surface or face 14, a top edge 16 that is rectangular and includes straight edges, a bottom edge 18 that is also rectangular and that includes straight edges. The splint body 12 includes a front face 14, a rear face 20, a left-hand side wall 21, a right-hand side wall 23, a top wall 25 and a bottom wall 27 connected together to form a block-shaped palm splint body 12, which is substantially a rectilinear solid and may, in fact be solid. The top edge 16 and the bottom edge 18 are both the same size and are superposed. The rear face 20, which is shown closer to the viewer to illustrate certain features that will be explained shortly, includes a convex curve that makes the splint body 12 progressively thicker at a uniform rate from the top rear edge 22 to the midpoint 24 between the top rear edge 22 and the bottom rear edge 26 and from the bottom rear edge 26 to the midpoint 24. This curved surface, that is, the rear face 20 will be pressed against the palm 28 of the patient (See FIG. 4) when the palm splint 10 is being used. The curvature of the rear face 20 is designed to fit comfortably into a patient's palm and reasonably conform to the shape of the palm when the hand is relaxed. The rear face 20 of the splint body 12 includes sixteen uniformly shaped and cells 30 arrayed in a rectangular block of four cells 30 by four cells 30 having two pairs of parallel sides forming a rectilinear shaped array or pattern, which open through the rear face 20 of the splint body 12. The cells 30 are basically voids that are included to reduce the amount of material used to make the splint body 12, which is preferably injection molded plastic, to provide for uniform cooling without warping after the splint body has been molded, and to reduce the weight of the splint body 12, thereby increasing the comfort to the patient. A significant marginal area 32 is provided between the perimeter 34 of the rear face 20 and the body of cells 30 to provide for sufficient strength in the completed splint body 12. The splint body 12 can be made from ally desirable type of material, such as stone, wood, and so forth and may be made from any desired process, such as carving, machining, and so forth.

Still referring to FIG. 1, a pad 36 having the same length and width as the front face 14 of the splint body 12 includes a rear face adhesive layer 38 applied uniformly on its rear face 40 and which allows the fabric pad 36 to be pressed against the rear face 14 of the splint body 12 and become permanently adhered thereto. The pad 36 is preferably made of fabric that forms a pad core 41, but can be made of any other suitable material, such as foam padding and may be permanently fixed to the front face 14 of the splint body 12 by any desired means. The front face 42 of the fabric pad is covered with pad loop connectors 44 which form half of a hook and loop type connector. Thus the principal purpose of the pad 36 is to provide a means for attaching the splint body 12 to the fastening strap 46.

Still referring to FIG. 1, a fastening strap 46 is a fabric strap having a fabric strap rear face 48 that is covered with the hook portion 50 of a hook and loop fastener system. On the left-hand end 52 of the strap front face 54 adjacent to the left-hand end 52 a patch of the loop portion 56 is permanently fastened by adhesive, sewing or the like. The pad loop connectors 44 are joined against the strap hook portion 50 at any convenient location along the fastening strap 46, thereby joining the fastening strap 46 and the splint body 12. The splint body 12 is then placed in the patient's palm and the fastening strap 46 is wrapped about the hand and the left-hand end 52 of the fastening strap 46 is secured to the right-hand end 58 of the fastening strap 46, with the hook portion 50 on the strap front face 54 of the hook and loop fastener engaging with the loop portion 50 on the fabric rear face 48. The fastening connection 60 (FIG. 4) of the fastening strap to itself may conveniently be placed directly over the front face 14 of the splint body 12, or may be placed at any convenient location along the length of the fastening strap 46.

Still referring to FIG. 1, a rear face pad 47 has the same length and width as the rear face 20 of the splint body 12 and includes a layer of adhesive 49 on its rear face, so that when the rear face pad 47 is pressed against the rear face 20 of the splint body 12, it will permanently adhere to the splint body 12, thereby covering the cells 30 and providing cushioning between the splint body 12 and the patient's palm 28. The rear face pad 47 includes a pad front face 51 covered with the hook portion 53 of a hook and loop fastener, allowing the palm splint to be reversed if desired, that is positioned with the front face 14 of the splint body 12 to be pressed against the patient's palm 28, as in some situations, it may be better to press a flat face, that is, front face 14, against the palm 28 than to press the rear face 20 of the splint body 12 against the palm 28.

Referring to FIG. 2, as shown there, the preferred position of the splint body 12 along the fastening strap 46 is centered along the length of the fastening strap 46. The width of the fastening strap 46 is the same as the width of the splint body 12.

Referring to FIG. 3, the cells 30 penetrate into the splint body 12 a sufficient distance so that the rear wall 62 of the splint body 12 has a thickness that is substantially the same as the perimeter 34, that is, the distance between the top edge 64, bottom edge 66, left-hand edge 68 and right-hand edge 70, all of the rear face 20, and the outer perimeter 72 of the block of cells 30.

Referring now to FIG. 4, the palm splint 10 is shown in use on a patient's hand with the front face 14 facing the viewer and the palm splint placed in the palm 28 below the lower bases 74 of the patient's fingers and above the base of the thumb 76.

The palm splint 10 may be made in a variety of sizes and with rear faces 20 having different curvatures. The palm splint may be made for different materials and, again, the cells 30 may be omitted when the palm splint 10 is made from a process other than injection molded plastic. Naturally, fasteners other than hook and loop fasteners may be used to fasten the splint to the hand. Alternatives include, for example, adhesive tape, tied straps, wide rubber bands and the like. The palm splint 10 may be used on either the right hand or the left hand of a patient without modification. The tightness of the strap and so the firmness with which the palm splint 10 presses into the palm can be readily adjusted by pulling harder or less hard on the fastening strap 46 prior to connecting the hook and loop fasteners of the fastening strap 46 together.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. A palm splint comprising a splint body, said splint body further comprising a three-dimensional splint body having a flat front face comprising a rectangle, a left-hand side wall, a right-hand side wall, a top wall and a bottom wall and a rear face comprising a curved convex surface adapted to be pressed against a user's palm when said palm splint is applied to said user, all connected together to form a block-shaped palm splint body and means for securing said splint body to the palm of a patient, wherein said securing means further comprises a Coextensive sheet of a loop portion of a hook and loop fastener system secured to said flat front face of said splint body by an adhesive, and a Coextensive sheet of a hook portion of a hook and loop fastener system secured to said rear face of said splint body by an adhesive and a separate and removable fastening strap having an inside face covered with a hook portion of a hook and loop fastener system whereby said strap can be readily connected to and disconnected from said front face of said splint body and an outer face of said fastening strap having two ends with a loop portion of a hook and loop fastener system attached to one said end of outer face of said strap whereby said strap can be connected to said flat front face of said splint body and, after being wrapped about the hand and to itself.

2. A palm splint in accordance with claim 1 wherein said splint body further comprises a plurality of cells arranged in an array having two pair of parallel sides forming a rectilinear pattern with each said cell comprising a square face penetrating into said splint body whereby the weight of said splint body is reduced, thereby increasing user comfort.

3. Am palm splint in accordance with claim 2 wherein said plurality of cells open through said rear face of said splint body and said array of cells is formed in an interior portion of said splint body and is surrounded by a marginal area between said array and a perimeter of said rear face whereby structural strength is retained in said splint body.

* * * * *